United States Patent

Piazza et al.

Patent Number: 5,565,439
Date of Patent: Oct. 15, 1996

[54] METHODS OF USING LYSOPHOSPHATIDIC ACID FOR TREATING HYPERPROLIFERATIVE CONDITIONS

[75] Inventors: Gary A. Piazza, West Chester; Adam W. Mazur, Cincinnati, both of Ohio

[73] Assignee: The Procter & Gamble Company, Cincinnati, Ohio

[21] Appl. No.: 334,888

[22] Filed: Nov. 4, 1994

Related U.S. Application Data

[63] Continuation of Ser. No. 980,814, Nov. 24, 1992, abandoned.

[51] Int. Cl.$^6$ ............................................. A61K 31/66
[52] U.S. Cl. .................... 514/110; 514/120; 514/859; 514/880; 558/86; 558/231; 560/264
[58] Field of Search ...................... 514/859, 880, 514/110, 120; 558/86, 231; 560/264

[56] References Cited

U.S. PATENT DOCUMENTS 4,876,381  10/1989  Lang et al. ................................. 560/56

FOREIGN PATENT DOCUMENTS

| | | | |
|---|---|---|---|
| 55-28955 | 2/1980 | Japan . | |
| 61-183207 | 8/1986 | Japan ................ | A61K 7/00 |
| 62-225240 | 10/1987 | Japan ................ | B01J 13/00 |
| 63-25342 | 8/1989 | Japan . | |
| 2-138132 | 5/1990 | Japan ................ | A61K 47/24 |
| 3-74316 | 3/1991 | Japan ................ | A61K 7/00 |
| 3-66604 | 3/1991 | Japan ................ | A61K 7/00 |
| 3-161414 | 7/1991 | Japan ................ | 514/859 |

OTHER PUBLICATIONS

Berdel, W., "Antineoplastic Activity of Synthetic Lysopholipid Analogs", *Blut*, vol. 44, pp. 71–78 (1982).

Glick, A., et al., "Retinoic Acid Induces Transforming Growth Factor-β2 in Cultured Keratinocycles and Mouse Epidermis", *Cell Regulation*, vol. 1, pp. 87–97 (1989).

Herrmann, D., et al., "Phase I Trial of the Thioether Phospholipid Analogue BM 41.440 in Cancer Patients", *Lipids*, vol. 22, pp. 954–962 (1987).

Lippmann, et al., "Recent Advances in Cancer Chemoprevention", *Cancer Cells*, vol. 3, pp. 59–65 (1991).

Moon, R., et al., "Retinoids and Cancer", *The Retinoids*, vol. 2, pp. 327–371 (1984).

Munder, P., et al., "Alkyllsyophospholipids in Cancer Therapy", *Augmenting Agents in Cancer Therapy*, pp. 441–458 (1981).

Piazza, G., et al., "Involvement of Transforming Growth Factor–Alpha in the Proliferative Response of Cultured Human Epidermal Cells to Retinoic Acid", *Clinical Research*, vol. 39, p. 519 (1991) (Abstract).

Sporn, M., "Carcinogensis and Cancer: Different Perspectives on the Same Disease", *Cancer Research*, vol. 51, pp. 6215–6218 (1991).

Sporn, M., et al., "Chemoprevention of Cancer with Retinoids", *Federation Proceedings*, vol. 38, pp. 2528–2534 (1979).

*Primary Examiner*—Shelley A. Dodson
*Attorney, Agent, or Firm*—John M. Howell; Milton B. Graff, IV; David L. Suter

[57] ABSTRACT

The subject invention involves a method for treating hyperproliferative conditions in mammalian epithelial cells comprising administering to the mammal a composition containing a safe and effective amount of a lysophosphatidic acid compound or derivative having the structure

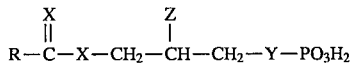

or a cyclic derivative thereof having the structure

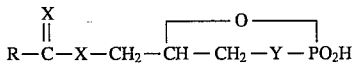

or a pharmaceutically acceptable salt thereof, wherein:

a) —Y— is —O— or —CH$_2$—;
b) —Z is —XH, —H or halo;
c) each —X— is independently —O— or —S—; and
d) —R is unsubstituted or substituted, saturated or unsaturated, straight or branched chain alkyl having from 11 to about 23 carbon atoms.

7 Claims, No Drawings

METHODS OF USING LYSOPHOSPHATIDIC ACID FOR TREATING HYPERPROLIFERATIVE CONDITIONS

This a continuation of application Ser. No. 07/980,814, filed on Nov. 24, 1992 abandoned.

TECHNICAL FIELD

The present invention relates to the prevention and treatment of conditions in mammals involving hyperproliferation of epithelial tissues. Specifically, the invention relates to non-cytotoxic methods for inhibiting epithelial cell proliferation. This invention is suitable for all benign and malignant conditions involving hyperproliferation of epithelial cells.

BACKGROUND OF THE INVENTION

Uncontrolled cell proliferation leads to numerous disease conditions. Some of the most severe consequences of hyperproliferation lead to malignant tumors, of which many can be life threatening. Other consequences of increased cell proliferation lead to benign conditions that cause mild to severe discomfort or pain, often requiring surgical and/or pharmacological intervention.

Both synthetic and naturally occurring retinoids are generally recognized to be effective for the prevention, as well as the treatment of a wide range of hyperproliferative conditions for dermatological and non-dermatological applications. Retinoids are believed to represent a physiological, rather than a cytotoxic, approach to arresting, reversing, or regulating hyperproliferation of epithelial cells. The fundamental theory underlying retinoid efficacy is the ability of retinoids to enhance normal physiological mechanisms which protect the organism against hyperplastic conditions. However, the therapeutic use of retinoids is limited due to poor efficacy and/or undesirable side effects.

Retinoids increase the production and secretion of the peptide growth factor, transforming growth factor, type beta (TGF-β) from human epidermal cells (Glick, et al., *Cell Regulation*, Vol. 1 (1989), pp. 87–97). This effect is important for certain therapeutic benefits of retinoids. TGF-β is produced by normal and malignant cells and is known to have a non-cytotoxic inhibitory effect on epithelial cell proliferation. Hyperproliferation of epithelial cells may involve a reduction of TGF-β levels in any given tissue compartment and/or a loss of sensitivity to target cells. Consequently, the induction of TGF-β secretion is significant in the prevention and treatment of cancer and broadly related non-malignant hyperproliferative conditions.

It is an object of the subject invention to provide methods for treating hyperproliferative conditions in mammals.

It is a further object of the subject invention to provide methods for the treatment and prevention of hyperproliferative conditions which are more efficacious and have fewer side effects than retinoids.

SUMMARY OF THE INVENTION

The subject invention involves a method for treating hyperproliferative conditions in mammalian epithelial cells comprising administering to a mammal susceptible to or having hyperproliferative conditions, a composition containing a safe and effective amount of a lysophosphatidic acid compound or derivative having the structure

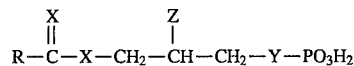

or a cyclic derivative thereof having the structure

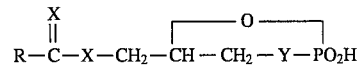

or a pharmaceutically acceptable salt thereof, wherein:
a) —Y— is —O— or —CH$_2$—;
b) —Z is —XH, —H or halo;
c) each —X— is independently —O— or —S—; and
d) —R is unsubstituted or substituted, saturated or unsaturated, straight or branched chain alkyl having from 11 to about 23 carbon atoms.

DETAILED DESCRIPTION OF THE INVENTION

In the subject invention, it has been found that the administration of compositions containing lysophosphatidic acid (LPA) derivatives is effective in treating hyperproliferative conditions in epithelial cells of mammals. LPA derivatives mimic the antiproliferative and TGF-β secretory properties of retinoids on epithelial cells and are therefore useful for treating a wide range of conditions including the hyperproliferation of epithelial cells. The subject invention is useful for all forms of cancers involving hyperproliferation of epithelium from skin, breast, prostate, bladder, intestine, lung, liver, uterus, esophagus, pancreas, etc. The invention is particularly well suited for the treatment of dermatological conditions involving hyperproliferation of epidermal cells which results in altered keratinization. These conditions include, but are not limited to, benign or malignant skin cancers, psoriasis, ichthiosis, seborreic keratosis, warts, eczema, or dandruff.

As used herein, "alkyl" means a substituted or unsubstituted carbon-containing chain which may be straight or branched; saturated, monounsaturated (i.e., one double or triple bond in the chain), or polyunsaturated (i.e., two or more double bonds in the chain; two or more triple bonds in the chain; one or more double and one or more triple bonds in the chain).

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein "treating hyperproliferative conditions" means preventing, retarding and arresting the process of hyperproliferation as well as healing conditions caused by hyperproliferation, by regulating cell differentiation.

Active Agent

The subject invention involves a method for treating hyperproliferative conditions in mammalian epithelial cells by administering to the mammal a safe and effective amount of a lysophosphatidic acid compound or derivative having the structure:

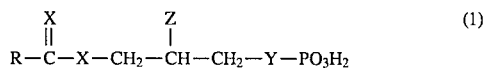

or a cyclic derivative thereof having the structure:

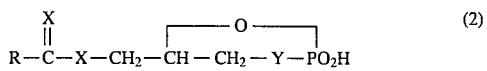

or a pharmaceutically-acceptable salt thereof, wherein:

a) —Y— is —O— or —$CH_2$—;
b) —Z is —XH, —H or halo;
c) each —X— is independently —O— or —S—; and
d) —R is unsubstituted or substituted, saturated or unsaturated, straight or branched chain alkyl having from about 11 to about 23 carbon atoms.

Structure (1) above is preferred.

Preferred —Y— is —O—.

Preferred —Z— is —H, —OH, —Cl or —F, especially —F.

Preferred —X— is —O—.

Preferred —R is straight chain.

Preferred —R has from about 13 to about 19 carbon atoms, more preferably from about 13 to about 17 carbon atoms.

Preferred —R is saturated or unsaturated with from one to about 3 double bonds, more preferably 1 or 2 double bonds, more preferably still one double bond; most preferred is —R being saturated.

Preferred —R is unsubstituted or substituted with halogen, hydroxy, phenyl, amino or acyl amino; more preferred —R is unsubstituted or substituted with halogen, especially —F, —Cl or hydroxy; most preferred —R is unsubstituted.

Particularly preferred is RC(O)O— being myristyl, palmityl, stearyl, palmitoleyl, oleyl or linoleyl; more preferably oleyl, palmitoleyl, myristyl, or palmityl; especially myristyl.

Structure (1) and (2) above can be in either D or L configuration or can be a mixture of D and L.

Preferred pharmaceutically-acceptable salts of lysophosphatidic acid compounds include alkali metal salts, such as sodium and potassium; alkaline earth metal salts, such as calcium and magnesium; non-toxic heavy metal salts; ammonium salts; and trialkylammonium salts, such as trimethylammonium and triethylammonium.

Preferred compounds useful in the methods and compositions of the subject invention include L and D 1-oleoyl glycerol-3-phosphate (oleyl lysophosphatidic acid), L and D 1-myristoyl glycerol-3-phosphate (myristyl lysophosphatidic acid), and L and D 1-palmitoyl glycerol-3-phosphate (palmityl lysophosphatidic acid), and salts thereof and mixtures thereof. Preferred compounds also useful in the methods and compositions of the subject invention include L and D 1-myristoyl-2-fluoro-2-deoxy-glycerol-3-phosphate, L and D 1-palmitoleyl-2-fluoro-2-deoxy-glycerol-3-phosphate, L and D 1-oleoyl-2-fluoro-2-deoxy-glycerol-3-phosphate, L and D 1-myristoyl-2-deoxy-glycerol-3-phosphate, L and D 1-oleoyl-2-chloro-2-deoxy-glycerol-3-phosphate, L and D 1-myristoyl-2-chloro-2-deoxy-glycerol-3-phosphate, and calcium salts thereof.

The following are non-limiting examples of the preparation of lysophosphatidic acid compounds useful in the subject invention.

EXAMPLE I

Preparation of 1-Oleoyl Glycerol-3-Phosphate

All glassware is oven dried. The reactions are run under nitrogen. To a solution of dibenzyl phosphite (78.8 mmole, 20.67 g) in $CCl_4$ (300 ml) is slowly added sulfuryl chloride (74 mmol, 9.99 g) in $CCl_4$ while the temperature is maintained at 16°–19° C. When the addition is complete, nitrogen is bubbled vigorously through the reaction mixture for 90 minutes and the solvent is evaporated. The oily residue is dissolved in $CCl_4$ and slowly added to a solution of 1,2-isopropylidene-sn-glycerol (Aldrich Chem. Co., 45 mmol, 6.0 g) in dry pyridine (15 ml) at 0° C. The reaction mixture is allowed to reach room temperature and is stirred for 1 hour. The precipitate of pyridinium chloride is filtered. The filtrate is diluted with chloroform (200 ml). The organic solution is extracted with 1N HCl (2×100 ml), aqueous sodium bicarbonate (100 ml) and water (100 ml). The organic layer is dried with anhydrous sodium sulfate and evaporated. The residue is chromatographed on a silica column using a solution of 50:50:1 hexanes:ethyl ether:acetic acid. The product is 1,2-isopropylidene-3-(O,O-dibenzylphosphate)-sn-glycerol (1).

Hydrolysis of the isopropylidene group in compound (1) is accomplished by mixing the substrate (5 g) with a solution of tetrahydrofuran (100 ml), 1N HCl (100 ml), and methanol (5 ml) at room temperature for 2.5 hours. After neutralization with 1N NaOH, the solvents are evaporated and the product is purified on a silica column. The product is 3-(O,O-dibenzylphosphate)-sn-glycerol (2).

A solution of oleic anhydride (11.4 mmol, 6.2 g) and 4-N,N-dimethylaminopyridine (DMAP) (0.57 mmol, 0.07 g) in dry methylene chloride (50 ml) is added to compound (2) (11.4 mmol, 4.0 g) in methylene chloride (100 ml) at 0° C. over a period of 2 hours. After mixing for an additional 2 hours at room temperature, the reaction mixture is washed with 1N HCl (100 ml) and evaporated. The crude product is purified on a silica column using for elution a solution of hexane:ethyl ether:acetic acid 50:50:1 (1000 ml), followed by a solution of hexane:ethyl ether:acetic acid 40:60:1. The product is 3-(O,O-dibenzylphosphate)-sn-1-oleoylglycerol (3).

It is important in the next step that reagents and vessels be absolutely dry, bromotrimethylsilane be of high purity (free from HBr and $Br_2$), and the reaction be run in an inert gas atmosphere. Compound (3) (4.86 mmol, 3.0 g) is dissolved in dry, alcohol-free chloroform (25 ml ). N,O-bis(trimethylsilyl ) trifluoroacetamide (Pierce Chem. Co., 14.6 mmol, 3.75 ml) is added followed by bromotrimethylsilane (Aldrich Chem. Co., 9.8 mmol, 1.3 ml). The reaction is complete after 5–10 minutes. The solvents are immediately evaporated. The residue is dissolved in acetone (9.5 ml) and treated with water (0.5 ml). The solvents are evaporated. The product is purified by silica gel chromatography using 4:1 chloroform:methanol. The product is 1-oleoyl glycerol-3-phosphate.

EXAMPLE II

Preparation of 1-0-Hexadecanoyl-1,2-Cyclic-sn-Glycerolphosphate

To a solution of 1-hexadecanoyl-sn-glycerol (Sigma Chem. Co., 0.76 mmol, 250 mg) in dry pyridine (5 ml) is added phosphorus oxychloride (1.13 mmol, 250 mg) at 0° C. After stirring at this temperature for 30 minutes, 1M sodium acetate (20 ml) is added and the mixture is kept overnight at 5° C. The precipitated product is filtered and dried over $P_2O_5$. The product is 1-0-hexadecanoyl-1,2-cyclic-sn-glycerolphosphate in the form of its sodium salt:

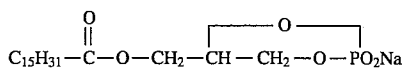

EXAMPLE III

Preparation of 3-Hydroxy-4-tetradecanoyloxyphosphonic Acid 1,2-Isopropylidene-glyceraldehyde prepared from 1,2-5,6-diisopropylidene mannitol (7.5 g) (Baer, E. & H. O. L. Fisher, *J. Biol. Chem.*, Vol. 128 (1939), pp. 463–473), is reacted with butyllithium (27.8 mmol, 11.1 ml) and tetraisopropyl methylenediphosphonate (27.6 mmol, 7.41 g) in heptane (150 ml) (Gupta, A., K. Sacks, S. Khan, B. E. Tropp & R. Engel, "An Improved Synthesis of Vinylic Phosphonates from Ketones", *Synthetic Communications*, Vol. 10, No. 4 (1980), pp. 299–304. The product is purified on a silica gel column to yield the unsaturated compound diisopropyl 3,4-dihydroxybuten-1-ylphosphonate, $HOCH_2—CHOH—CH=CH—P(O)—(OCH(CH_3)_2)_2$, which is hydrogenated at atmospheric pressure using 10% $Pd(OH)_2$ on charcoal (1.0 g) in 95% MeOH (100 ml). The product is diisopropyl 3,4-dihydroxybutylphosphonate (4).

Compound (4) (500 mg) is stirred with myristic acid anhydride (2.17 g) and lipozyme (2 g) in methylene chloride (50 ml) at room temperature for 2 hours. The enzyme is removed by filtration. The filtrate is evaporated and the product, 3-hydroxy-4-tetradecanoyloxybutylphosphonate (5), is purified on a silica column using 50:50:1 hexane:ethyl acetate:acetic acid. Compound (5) (0.432 mmol, 0.2 g) is dissolved in dry, alcohol-free chloroform (2 ml). N-O-bis(trimethylsilyl) trifluoroacetamide (0.9 mmol, 0.2 ml) is added, followed by addition of bromotrimethylsilane (1.3 mmol, 0.17 ml) from a syringe over a period of 1 hour. The reaction is complete after 6 hours. The solvents are evaporated. The residue is dissolved in acetone (2 ml) and treated with water (0.2 ml). The product, 3-hydroxy-4-tetradecanoyloxyphosphonic acid, crystallizes upon cooling.

EXAMPLE IV

Preparation of 1-Myristoyl-2-Fluoro-2-Deoxyglycerol-3-Phosphate

Methylene chloride is dried by distillation from $P_2O_5$. Acetonitrile is distilled from $CaH_2$. All the reagents are purchased from Aldrich Chemical Co. Thin layer chromatography (TLC) is performed on Analtech silica gel G60 plates activated in the oven at 120° C. The nmr spectra are obtained on a Brucker 300 MHz spectrometer.

3-Bromo-2-fluoro-1-propanol (2): To a solution of dry methylene chloride (30 ml) and N-bromosuccinimide (NBS) (87 mmole, 15.45 g) at 0° C. is slowly added triethylamine trihydrofluoride (157 mmole, 25 g) and allyl alcohol (77 mmole, 4.5 g). The mixture is allowed to warm to +10° C. and is stirred until the NBS dissolves (approx. 5 hours). The reaction mixture is treated with ice-cold water (300 ml) and extracted with ethyl ether (2×50 ml). The organic phase is successively washed with aq. $NaHCO_3$ solution (100 ml), water (100 ml), and is dried with anhydrous $MgSO_4$. Solvent is evaporated in the stream of air at room temperature in the hood. Upon distillation of the residue, four fractions are collected: 76°–79° C. (0.63 g), 79°–81° C., (0.34 g), 82°–88° C. (0.50 g), 89°–101° C. (0.52 g). The carbon nmr analysis shows that all fractions contain product (2) as the major component with only small amounts of unidentified impurities. All four fractions are combined. Yield is 1.99 g of (2).

3-Bromo-2-fluoro-1-tetradecanoyloxypropane(3): A solution of 3-Bromo-2-fluoro-1-propanol (2) (53 mmole, 8.3 g), tetradecanoyl anhydride (63.4 mmole, 27.8 g), 4-N,N-dimethylaminopyridine (63.4 mmole, 0.78 g) in dry methylene chloride (50 ml) is stirred at room temperature for 2 hours. The solution is washed with 1N HCl (2×500 ml) and aqueous sodium bicarbonate. The latter treatment causes precipitation of sodium tetradecanoate which is removed by filtration. The filtrate is washed with water, dried with anhydrous $Na_2SO_4$, and evaporated, giving 9.6 g of product (3).

Silver dibenzyl phosphate: Dibenzyl phosphate (10 mmole, 2.78 g) is dissolved in a mixture of acetonitrile (20 ml) and water (10 ml). Silver carbonate (10 mmole, 2.76 g) is added, and the mixture is stirred at room temperature in the dark (wrapped in aluminum foil) for 2 hours. Excess of silver carbonate is removed by filtration. The solution is evaporated to dryness, and dried over $P_2O_5$ in the dark to constant weight (2 days). Yield of silver dibenzoyl phosphate is 3.61 g.

1-Myristoyl-2-fluoro-2-deoxy-glycerol-3-dibenzylphosphate (4): 3-Bromo-2-fluoro-1-tetradecanoyloxypropane (3) (28.6 mmole, 9.6 g) and silver dibenzyl phosphate (60 mmole, 23.1 g) are stirred in dry acetonitrile (200 ml) at 80° C. for 24 hours. The reaction mixture is filtered; the solution is evaporated to dryness. The residue is dissolved in a small volume of AcOEt; precipitate is removed by filtration. The filtrate is chromatographed on a silica column using initially a solution of ethyl acetate, hexane, AcOH 20:80:1 as the mobile phase, followed by elution with ethyl acetate. The fractions containing product (4) are pooled, concentrated, and dissolved in benzene. The benzene solution is washed with aq. $NaHCO_3$ and water, and is dried with anhydrous $Na_2SO_4$. Evaporation gives 1.9 g of product (4).

1-Myristoyl-2-fluoro-2-deoxy-glycerol-3-phosphate (5): Product (4) is hydrogenated in 70% aqueous ethanol (50 mL) in the presence of palladium hydroxide on charcoal (0.4 g) overnight under normal conditions. The catalyst is removed by filtration. The residue on the filter is washed with hot methanol. Evaporation of the filtrate gives 1.3 g of product (5).

Pharmaceutically-Acceptable Carrier

In addition to the active agent as described hereinbefore, the pharmaceutical compositions of the present invention essentially comprise a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being commingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogenfree water; isotonic saline; phosphate buffer solutions; cocoa butter (suppository base); emulsifiers, such as the Tweens®; as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., NSAID drugs; pain killers; muscle relaxants) may be included in the pharmaceutically-acceptable carrier for use in the compositions of the present invention. For example, art-known local anesthetics may be included in the pharmaceutically-acceptable carrier (e.g., benzyl alcohol; Novocaine®; lidocaine).

The choice of a pharmaceutically-acceptable carrier to be used in conjunction with the compounds of the present invention is basically determined by the way the compound is to be administered. The preferred modes of administering the compounds of the present invention are by injection, orally and topically. If the compound is to be injected, the preferred pharmaceutically-acceptable carrier is sterile, physiological saline. Suitable pharmaceutically-acceptable carriers for topical application include those suited for use in creams, gels, tapes and the like; and for oral administration include those suited for tablets and capsules.

The pharmaceutically-acceptable carrier employed in conjunction with the compounds of the present invention is used at a concentration sufficient to provide a practical size to dosage relationship. The pharmaceutically-acceptable carriers, in total, may comprise from about 0.1% to about 99.99999% by weight of the pharmaceutical compositions of the present invention, preferably from about 80% to about 99.99%, more preferably from about 90% to about 99.95%, even more preferably from about 95% to about 99.9%, also preferably from about 98% to about 99%.

Total single dosages of the compounds of the present invention present in pharmaceutical compositions herein are generally from about 1 µg to about 10 g. Preferred single dosages are from about 1 mg to about 3500 mg; more preferred are from about 10 mg to about 1000 mg; and most preferred are from about 100 mg to about 600 mg.

Specific oral, topical, and injectable carrier formulations useful in this invention are described in the following U.S. Patents, all incorporated by reference herein: U.S. Pat. No. 4,401,663, Buckwalter, et al, issued Aug. 30, 1983; U.S. Pat. No. 4,424,205, LaHann, et al, issued Jan. 31, 1984; U.S. Pat. No. 4,443,473, Buckwalter, et al, issued Apr. 12, 1984; U.S. Pat. No. 4,493,848, LaHann, et al, issued Jan. 15, 1984. Representative compositions of the subject invention are provided in the Examples hereinafter.

Pharmaceutically-acceptable carriers suitable for the preparation of unit dosage forms for oral administration and injection, and dosage forms for topical application are well-known in the art. Their selection will depend on secondary considerations like taste, cost, and/or shelf stability, which are not critical for the purposes of the subject invention, and can be made without difficulty by a person skilled in the art. Pharmaceutically-acceptable carriers useful in the compositions of the subject invention are described more fully hereinafter.

A. Oral Dose Forms:

Various oral dosage forms can be used, including such solid forms as tablets, capsules, granules, bulk powders and micro-capsules of the drug. These oral forms comprise a safe and effective amount, usually at least about 5%, and preferably from about 25% to about 50% of the compound of the subject invention. Tablets can be compressed, enteric-coated, sugar-coated or film-coated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin and propylene glycol. Specific examples of pharmaceutically-acceptable carriers and excipients that may be used in formulating oral dosage forms containing compounds of the subject invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated herein by reference. Techniques and compositions for making tablets (compressed, formulas and molded), capsules (hard and soft gelatin) and pills are described in *Remington's Pharmaceutical Sciences*(Arthur Osol, editor), 1553–1593 (1980), incorporated herein by reference.

The preferred unit dosage form for oral administration is tablets, capsules and the like, comprising a safe and effective amount of a compound of the subject invention. Preferably oral dose forms comprise from about 10 mg to about 3500 mg of a compound of the subject invention, more preferably from about 25 mg to about 1000 mg, and most preferably from about 50 mg to about 600 mg.

B. Injectable Dose Forms:

The compounds of the subject invention are also useful when injected. The dosage of the compound of the subject invention which is both safe and effective to treat hyperproliferative conditions in mammalian epithelial cells will vary with the particular condition being treated, the severity of the condition, the duration of treatment, the specific compound employed and its usage concentration, and like factors within the specific knowledge and expertise of the attending physician and commensurate with a reasonable benefit/risk ratio associated with the use of any drug compound. The injectable dosages and dosage ranges given herein are based on delivery of the compound of the subject invention to a 70 kg human and can be adjusted to provide equivalent dosages for patients of different body weights.

Methods and materials for manufacturing injectables can be found in *Remington's Pharmaceutical Science,* 17ed., 1985, Chapter 85, p. 1518, the disclosures of which are incorporated herein by reference in their entirety. Materials for use in injectables are also described more fully hereinafter.

Generally, three types of injectable dosage forms are preferred: 1) aqueous solutions; 2) non-aqueous solutions; and 3) emulsions. The above dosage forms typically contain from about 0.001 mg/ml to about 10 mg/ml, preferably from about 0.1 mg/ml to about 1 mg/ml, more preferably from about 0.4 mg/ml to about 0.6 mg/ml, of the compound of the subject invention.

C. Topical Dose Form:

The compositions of the subject invention can also be administered topically to a biological subject, i.e., by the direct laying on or spreading of the composition on epithelial tissue.

The topical compositions useful in the subject invention involve compositions suitable for topical application to mammalian skin, the composition comprising a safe and effective amount of an active agent for the treatment of hyperproliferation or mixture of such actives as described hereinabove, and a pharmaceutically-acceptable topical carrier. The subject compositions preferably contain from about 0.01% to about 20%, preferably from about 0.05 to about 5%, more preferably from about 0.1% to about 2%, also preferably from about 1% to about 2% of the active agent.

The topical compositions useful in the subject invention may be made into a wide variety of product types. These include, but are not limited to lotions, creams, beach oils, gels, sticks, sprays, ointments, pastes, mousses, cosmetics, shampoos, cream rinses, hair tonics and hair conditioners. These product types may comprise several types of carrier systems including, but not limited to solutions, emulsions, gels, solids, and liposomes.

The topical compositions useful in the subject invention formulated as solutions typically include a pharmaceutically-acceptable aqueous or organic solvent. Water is a preferred solvent. Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, ethanol, isopropanol, butanediol, and mixtures thereof. These solutions useful in the subject invention preferably contain from about 01% to about 20%, more preferably from about 1% to about 5% of the active agent for the treatment of hyperproliferation, and preferably from about 80% to about 99.99%, more preferably from about 90% to about 99% of an acceptable aqueous or organic solvent.

Aqueous containing topical compositions of the subject invention preferably contain a calcium chelator to prevent precipitation of insoluble salts of lysophosphatidic acid compounds. Preferred calcium chelators include ethylenediaminetetraacetic acid (EDTA) and ethylene glycol bis(β-aminoethyl ether)-N,N,N',N'-tetraacetic acid (EGTA).

If the topical-compositions useful in the subject invention are formulated as an aerosol and applied to the skin as a spray-on, a propellant is added to a solution composition. Examples of propellants is added to a solution composition. Examples of propellants useful herein include, but are not limited to, the chlorinated, fluorinated an chloro-fluorinated lower molecular weight hydrocarbons. A more complete disclosure of propellants useful herein can be found in Sagarin, *Cosmetics Science and Technology,* 2nd Edition, Vol. 2, pp. 443–465 (1972)

Topical compositions useful in the subject invention may be formulated as a solution comprising an emollient. An example of a composition formulated in this way would be a beach oil product. Such compositions preferably contain from about 0.05% to about 5% of an active agent and from about 2% to about 50% of a topical pharmaceutically-acceptable emollient. Such compositions preferably comprise a lipid soluble salt of a subject active agent, such as a calcium salt.

As used herein, "emollients" refer to materials used for the prevention or relief of dryness, as well as for the protection of the skin. A wide variety of suitable emollients are known and may be used herein. Sagarin, *Cosmetics, Science and Technology,* 2nd Edition, Vol. 1, pp. 32–43 (1972), incorporated herein by reference, contains numerous examples of suitable materials.

A lotion can be made from a solution carrier system. Lotions typically comprise from about 0.01% to about 20%, preferably from about 1% to about 10%, of the active agent for the treatment of hyperproliferation; from about 1% to about 20%, preferably from about 5% to about 10%, of an emollient; and from about 50% to about 90%, preferably from about 60% to about 80%, water.

Another type of product that may be formulated from a solution carrier system is a cream. A cream typically comprises from about 0.01% to about 20%, preferably from about 1% to about 10%, of the active agent; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons oleaginous). Ointments may also comprise absorption ointment bases which absorb water to form emulsions. Ointment carriers may also be water soluble. An ointment may also comprise from about 0.01% to about 20% of an active agent and from about 2% to about 10% of an emollient and from about 0.1% to about 2% of a thickening agent. A more complete disclosure of thickening agents useful herein can be found in Sagarin, *Cosmetics, Science and Technology,* 2nd Edition, Vol. 1, pp. 72–73 (1972).

If the carrier is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al.,; U.S. Pat. No. 4,421,769, issued Dec. 20, 1983, Dixon et al.; and McCutcheon's *Detergents and Emulsifiers,* North American Edition, pages 317–324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about 0.01% to about 20%, preferably from about 1% to about 10%, of the active agent; from about 1% to about 20%, preferably from about 5% to about 10%, preferably from about 0.5% to about 5%, of an emulsifier. Such creams would typically comprise from about 0.01% to about 20%, preferably from about 0.1% to about 10%, of the active agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. No.

4,254,105, Fakuda et al., issued March 3, 1981, incorporated herein by reference, are also useful in the subject invention. In general, such single or multiphase emulsions contain water, emollients and emulsifiers as essential ingredients.

Triple emulsion carrier systems comprising an oil-in-water-in-silicone in-silicone fluid emulsion composition as disclosed in U.S. Pat. No. 4,960,764, Figueroa, issued Oct. 2, 1990, are also useful in the subject invention. This triple emulsion carrier system is preferably combined with from about 0.01% to about 20%, more preferably combined from about 0.1% to about 10%, of the active agent to yield a topical composition useful in the subject invention.

Another emulsion carrier system useful in the topical compositions is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is preferably combined with from about 0.1% to about 10% of the active agent.

Liposomal formulations are also useful compositions of the subject invention. Such compositions can be prepared by first combining an active agent with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", *Journal of Pharmaceutics and Pharmacology*, Vol. 34 (1982), pp. 473–474, incorporated herein by reference, or a modification thereof. Epidermal lipids of suitable composition for forming liposomes may be substituted for the phospholipid. The liposome preparation is then incorporated into one of the above topical carrier systems (for example, a gel or an oil-in-water emulsion) in order to produce the liposomal formulation. The final formulation preferably contains from about 0.1% to about 10%, more preferably from about 0.1% to about 5%, of the active agent. Other compositions and pharmaceutical uses of topically applied liposomes are described in Mezei, M., "Liposomes as a Skin Drug Delivery System", *Topics in Pharmaceutical Sciences* (D. D. Breimer and P. Speiser, eds.,), Elsevier Science Publishers B. V., New York, N.Y., 1985, pp. 345–358, incorporated herein by reference.

If the topical compositions useful in the subject invention are formulated as a gel or a cosmetic stick, such compositions can be formulated by the addition of a suitable amount of a thickening agent, as disclosed supra, to a cream or lotion formulation.

The topical compositions useful in the subject invention may contain, in addition to the aforementioned components, a wide variety of additional oil-soluble materials and/or water-soluble materials conventionally used in topical compositions, at their art-established levels.

Various water-soluble materials may also be subject in the compositions useful in the subject invention. These include humectants, proteins and polypeptides, preservatives and an alkaline agent. In addition, the topical compositions useful herein can contain conventional cosmetic adjuvants, such as dyes, opacifiers (e.g. titanium dioxide), pigments and perfumes.

The topical compositions useful in the subject invention may also include a safe and effective amount of penetration enhancing agent. A preferred amount of penetration enhancing agent is from about 1% to about 5% of the composition. Examples of useful penetration enhancers, among others, are disclosed in U.S. Pat. No. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and 4,954,487, Cooper, Loomans & Wickett, issued Sep. 4, 1990. Additional penetration enhancers useful in the subject invention are disclosed in Cooper, E. R., "Effect of Decylmethylsulfoxide on Skin Penetration", *Solution Behavior of Surfactants*, Vol 2 (Mittal and Fendler, eds.), Plenum Publishing Corp., 1982, pp. 1505–1516; Mahjour, M., B. Mauser, Z. Rahidbaigi & M. B. Fawzi, "Effect of Egg Yolk Lecithins and Commercial Soybean Lecithins on In Vitro Skin Permeation of Drugs", *Journal of Controlled Release*, Vol. 14 (1990), pp. 243–252; Wong, O., J. Huntington, R. Konishi, J. H. Rytting & T. Higuchi, "Unsaturated Cyclic Ureas as New Nontoxic Biodegradable Transdermal Penetration Enhancers I: Synthesis", *Journal of Pharmaceutical Sciences*, Vol 77, No 11 (Nov. 1988), pp. 967–971; Williams, A. C. & B. W. Barry, "Terpenes and the Lipid-Protein-Partitioning Theory of Skin Penetration Enhancement", *Pharmaceutical Research*, Vol. 8, No. 1 (1991), pp. 17–24; and Wong, O., J. Huntington, T. Nishihata & J. H. Rytting, "New Alkyl N,N-Dialkyl-Substituted Amino Acetates as Transdermal Penetration Enhancers", *Pharmaceutical Research*, Vol. 6, No. 4 (1989), pp. 286–295. The above references are incorporated herein by reference.

Other conventional skin care product additives may also be included in the compositions useful in the subject invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions useful in the subject invention. For example, Vitamin A, and derivatives thereof, Vitamin B2, biotin, pantothenic, Vitamin D, and mixtures thereof may be used.

Cleaning Compositions

Skin cleaning compositions useful in the subject invention comprise, in addition to the active agent, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being comingled with the active agent in a manner such that there is no interaction which would substantially reduce the efficacy of the composition for treating hyperproliferative conditions in mammalian epithelial cells.

The skin cleaning compositions useful in the subject invention preferably contain from about 0.01% to about 20%, more preferably from about 0.1% to about 5%, of the active agent and preferably from about 1% to about 90%, more preferably from about 5% to about 10%, of a cosmetically-acceptable surfactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions useful in the subject invention are selected from anionic, nonionic, zwitterionic, amphoteric and ampholytic surfactants, as well as mixtures of these surfactants. Such surfactants are well-known to those skilled in the detergency art.

The cleaning compositions useful in the subject invention can optionally contain, at their art-established levels, materials which are conventionally used in skin cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, *Detergents and Emulsifiers*, North American Edition (1986), published by Allured Publishing Corporation, which is incorporated herein by reference in its entirety.

Combination Actives

A. Sunscreens and Sunblocks

Treatment of hyperproliferation can be achieved by using combinations of the active agents together with sunscreens or sunblocks. Useful sunblocks include, for example, zinc oxide and titanium dioxide. The combination of an active agent, with a UVA and/or UVB sunscreen is desirable. The inclusion of sunscreens in compositions useful in the subject invention at low levels does not greatly reduce the tanning response of the user but enhances immediate protection against acute UV damage, a predominant cause of hyperproliferation.

A wide variety of conventional sunscreening agents are suitable for use in combination with the active LPA derivative agent. Segarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxybiphenyldisulfonates; coumarin derivatives (7-hydroxy, 7-methyl, 3-phenyl ); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2', 4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; and 4-isopropyl-dibenzoylmethane.

Of these, 2-ethylhexyl-p-methoxycinnamate, 4,4'-t-butyl methoxydibenzoylmethane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethylamino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used in the compositions useful in the subject invention. The sunscreening agent must be compatible with the active agent. The composition preferably comprises from about 1% to about 20%, more preferably from about 2% to about 10%, of a sunscreening agent. Exact amounts will vary depending upon the sunscreen chosen and the desired Sun Protection Factor (SPF) .

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred composition useful in the subject invention, an anti-inflammatory agent is included as an active along with the active agent. The inclusion of an anti-inflammatory agent enhances the benefits of the compositions in treating hyperproliferation. The anti-inflammatory agent protects strongly in the UVA radiation range (though it also provides some UVB protection as well). (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal antiinflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Antiinflammatory and Anti-Rheumatic Drugs*, K. D. Rainsford, Vol. I–III, CRC Press, Boca Raton, (1985) , and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trillsate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6 -di-t-butylphenol; 4-((S)-(−)-3'-methyl-5'-hexynoyl)-2,6-di-t-butyphenol; 4-((R)-(+)-3'-methyl-5'-hexynoyl)-2,6-di-t-butylphenol; and 4-(3', 3'-dimethoxypropionyl)-2,6-di-t-butylphenol are useful in methods of the subject invention; 4-(5'-hexynoyl)-2,6-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the subject invention.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia cordifolia*), and Guggal (extracted from plants in the genus Commiphora, particularly *Commiphora mukul*), may be used.

Another preferred composition useful in the subject invention comprises an active LPA derivative agent, a sunscreen, and an anti-inflammatory agent together for treatment of hyperproliferation in the amounts disclosed for each individually hereinabove.

C. Anti-Oxidants/Radical Scavengers

In a preferred composition useful in the subject invention, an anti-oxidant/radical scavenger is included as an active along with the LPA derivative. The inclusion of an anti-oxidant/radical radical scavenger increases the benefits of the composition in treating hyperproliferation.

A safe and effective amount of an anti-oxidant/radical scavenger may be added to the compositions useful in the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

In a preferred composition useful in the subject invention, compositions comprise one, any two, or all three of a sun-screening agent, anti-inflammatory agent, and/or an anti-oxidant/radical scavenging agent included as actives along with the active LPA derivative. The inclusion of two or all three of these agents with the active LPA derivative increases the benefits of the composition in treating hyperproliferation.

D. Chelators

In a preferred composition useful in the subject invention, a chelating agent is included as an active along with the LPA derivative. As used herein, "chelating agent" means an active agent capable of removing a metal ion from a system by forming a complex so that the metal ion cannot readily participate in or catalyze chemical reactions. The inclusion of a chelating agent increases the benefits of the composition in treating hyperproliferation.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. Pat. application Ser. 514,892, Bush & Bissett, filed Apr. 26, 1990; U.S. patent application Ser. No. 657,847, Bush, Bissett & Chatterjee, filed Feb. 25, 1991; and U.S. patent application Ser. No. 776,506, Bush, filed Oct. 11, 1991; all incorporated herein by reference. Preferred chelators useful in compositions of the subject invention are furildioxime and derivatives thereof.

In a preferred composition useful in the subject invention, compositions comprise one, any two, any three, or all four of a sunscreening agent, anti-inflammatory agent, anti-oxidant/radical scavenging agent, and/or chelating agent included as actives along with the LPA derivative. The inclusion of two, three, or all four of these agents with the active agent increases the benefits of the composition in treating hyperproliferation.

E. Retinoids

In a preferred composition useful in the subject invention, a retinoid, preferably retinoic acid, is included as an active along with the LPA derivative. The inclusion of a retinoid increases the benefits of the composition in treating hyperproliferation. A safe and effective amount of a retinoid may be added to the compositions useful in the subject invention, preferably from about 0.001% to about 1%, more preferably from about 0.01% to about 0.05% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

In a preferred composition useful in the subject invention, compositions comprise one, any two, any three, any four, and/or all five of a sunscreening agent, anti-inflammatory agent, anti-oxidant/radical scavenging agent, chelating agent, and/or a retinoid included as actives along with the LPA derivative. The inclusion of two, three, four, or all five of these agents with the LPA derivative increases the benefits of the composition in treating hyperproliferation.

F. Chemopreventive Agents

In a preferred composition for the treatment of hyperproliferation, a chemopreventive agent is included as an active along with the LPA derivative active agent. For a disclosure of preferred chemopreventive agents, see Lippman, S., W. Hittelman, R. Lotan, U. Pastorino & W. K. Wong, "Recent Advances in Cancer Chemoprevention", *Cancer Cells*, Vol. 3, No. 2 (February, 1991), pp. 59–65, incorporated herein by reference. Chemopreventive agents preferred in the subject invention include N-acetyl cysteine, β-glycyrrhetinic acid, soybean-derived protease inhibitor (Bowman-Birk), selenium, sodium molybdate, ellagic acid, oltipraz, dehydroepiandrosterone, 2-difluoromethylornithine, piroxicam and all-trans-N-4-(hydroxyphenyl) retinamide.

The inclusion of a chemopreventive agent increases the benefits of the composition in treating hyperproliferation. A safe and effective amount of a chemopreventive agent may be added to the compositions useful in the subject invention, preferably from about 0.001% to about 2%, more preferably from about 0.01% to about 1% of the composition. As used herein, "chemopreventive agent" includes all natural and/or synthetic analogs capable of inhibition or reversal of carcinogenesis, primarily in the premalignant phase. Chemopreventive agents are also useful in preventing the initiation of pre-malignant events.

In a preferred composition useful in the subject invention, compositions comprise one, any two, any three, any four, any five, and/or all six of a sunscreening agent, anti-inflammatory agent, anti-oxidant/radical scavenging agent, chelating agent, retinoid, and/or a chemopreventive agent included as actives along with the LPA derivative. The inclusion of two, three, four, five or all six of these agents with the LPA derivative increases the benefits of the composition in treating hyperproliferation.

G. Chemotherapeutic Agents

In a preferred composition for the treatment of hyperproliferation and chemotherapeutic agent is included as an active along with the LPA derivative agent. Preferred chemotherapeutic agents useful in the subject invention include: alkylating agents, including nitrogen mustards such as mechlorethamine (mustargen, $HN_2$, nitrogen mustard), cyclophosphamide (cytoxan, endoxam), chlorambucil (leukeran), and melphalan (alkeran, L-PAM, L-phenylalanine mustard); alkyl sulfonates such as busulfan (myleran); nitrosoureas such as carmustine (BCNU, BiCNU), Lomustine (CCNU, CeeNU), semustine (methyl-CCNU), and streptozocin (zanosar, streptozotocin); ethylenimines such as thiotepa; triazenes such as dacarbazine (DTIC); antimetabolites, including folate antagonists such as methotrexate (amethopterin); purine analogues such as thioguanine (6TG, 6-thioguanine), and mercaptopurine (6MP, purinethol); pyrimidine analogues such as cytarabine (cytosine arabinoside, cytosar, ara-C), and fluorouracil (5-FU, 5-fluorouracil); antibiotics including anthracyclines such as doxorubicin (adriamycin), and daunorubicin (daunomycin); bleomycins such as bleomycin (blenoxane); mitomycin (mitomycin C; mutamycin); dactinomycin (actinomycin-D, cosmegan); and mithramycin (mithracin); vinca alkaloids such as vincristine (oncovin), and vinblastine (velban); enzymes such as L-asparaginase (Elspar); hormones such as glucocorticoids; estrogens; androgens, progestins; antiestrogens such as tamoxifen (nolvadex); and miscellaneous agents such as hydroxyurea (hydrea), procarbazine (N-methylhydrazine, matulane, natulan); mitotane (o,p'-DDD, lysodren), hexamethylmelamine (HMM), cisplatin (cis-platinum II; CDDP), and etoposide (VP-16–213). (Proprietary and other names are in parentheses).

The inclusion of a chemotherapeutic agent increases the benefits of the composition in treating hyperproliferation. A safe and effective amount of a chemotherapeutic agent may be added to the compositions useful in the subject invention, preferably from about 0.001% to about 2%, more preferably from about 0.01% to about 1% of the composition. As used herein, "chemotherapeutic agent" includes all natural and/or synthetic analogs capable of eradication of existant malignancy by a cytotoxic action in malignant cells.

In a preferred composition useful in the subject invention, compositions comprise one, any two, any three, any four, any five, any six and/or all seven of a sunscreening agent, anti-inflammatory agent, anti-oxidant/radical scavenging agent, chelating agent, retinoid, chemopreventive agent and/or a chemotherapeutic agent included as actives along with the LPA derivative. The inclusion of these agents with the LPA derivative increases the benefits of the composition in treating hyperproliferation.

H. Anti-Fungal Agents

In a preferred composition for the treatment of dandruff, an anti-fungal agent is included as an active along with the LPA derivative agent. As used herein, "anti-fungal agent" means any compound antagonistic to fungi; or capable of damaging cell walls of fungi; or causing chemicals essential for normal function and growth of fungi to escape from the cell wall.

A preferred anti-fungal agent useful in the subject invention is zinc pyridinethione. For a more complete disclosure of the use of zinc pyridinethione, see U.S. Pat. No. 4,345,080, Bolich, R., issued Aug. 17, 1982; incorporated herein by reference.

The inclusion of an anti-fungal agent increases the benefits of the composition in treating dandruff. A safe and effective amount of an anti-fungal agent may be added to the compositions useful in the subject invention, preferably from about 0.001% to about 4%, more preferably from about 0.3% to about 3% of the composition, also preferably from about 1% to about 2% of the composition.

Methods for Treating Hyperproliferation in Mammals

The subject invention relates to methods for treating hyperproliferation in mammalian epithelial cells. Such methods comprise topical application of a safe and effective amount of an active agent. The amount of treatment and frequency of application will vary widely depending upon the conditions of the epithelial cells already in existence in the subject, the rate of further cell proliferation, and the level of regulation desired. Preferred treatment of hyperproliferation involves preventing or retarding the hyperproliferation of epithelial cells. More preferred treatment of hyperproliferation involves reversing the condition in existing epithelial cells.

A safe and effective amount of active agent in a topical composition is applied, generally from about 0.001 mg to about 2 mg per $cm^2$ skin per application, preferably from about 0.01 mg to about 1 mg per $cm^2$ skin per application, also preferably from about 0.05 mg to about 0.5 mg/$cm^2$. For preventing or retarding the onset of hyperproliferation, application preferably ranges from about monthly to about 5 times daily, more preferably from about biweekly to about daily, more preferably still from about weekly to about 3 times per week.

A preferred method of the subject invention for treating hyperproliferation in mammalian skin involves applying both a safe and effective amount of the active LPA derivative and a safe and effective amount of one or more of a sunscreening agent, an anti-inflammatory agent, an anti-oxidant/radical scavenging agent, a chelating agent, a retinoid, a chemopreventive agent and/or a chemotherapeutic agent to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is preferably from about 0.05 mg to about 0.5 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of anti-oxidant/radical scavenging agent preferably applied is from about 0.01 mg to about 1.0 mg, more preferably from about 0.05 mg to about 0.5 mg per $cm^2$ skin. The amount of chelating agent preferably applied is from about 0.001 mg to about 1.0 mg, more preferably from about 0.01 mg to about 0.5 mg, still more preferably from about 0.05 mg to about 0.1 mg per $cm^2$ skin. The amount of retinoid applied is preferably from about 0.001 mg to about 0.5 mg per $cm^2$ skin, more preferably from about 0.005 mg to about 0.1 mg per $cm^2$ skin. The amount of chemopreventive agent preferably applied is from about 0.001% mg to about 1.0 mg, more preferably from about 0.05 mg to about 0.1 mg per $cm^2$ skin. The amount of chemotherapeutic agent preferably applied is from about 0.001 mg to about 2 mg per $cm^2$ skin per application, more preferably from about 0.01 mg to about 1 mg per $cm^2$ skin per application. The amount of the active LPA derivative applied is preferably from about 0.001 mg to about 2 mg per $cm^2$ skin per application, more preferably from about 0.01 mg to about 1 mg per $cm^2$ skin per application.

The preferred modes of administration are orally, topically, including, e.g., dermatomucosally (for example, dermally, rectally and the like), and parenterally (for example, by subcutaneous injection, intramuscular injection, intra-articular injection, intravenous injection and the like). Thus, specific modes of administration include, without limitation, oral, transdermal, mucosal, sublingual, intramuscular, intravenous, intraperitoneal, and subcutaneous administration, as well as topical application.

Oral administration can be used to reduce hyperproliferation through oral dosing of a pharmaceutical composition comprised of a safe and effective amount of the compound of the subject invention in a suitable oral pharmaceutical carrier. The compound is absorbed by the gastrointestinal tract. The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

The amount of the compound ingested depends upon the bio-availability of the compound from the oral pharmaceutical composition. Typically, however, the compounds of the subject invention are dosed in an amount of from about 0.1 mg/kg of body weight to about 500 mg/kg, and preferably from about 1 to about 100 mg/kg of body weight. The amount of the pharmaceutical composition depends upon the percent of compound within its formula, which is a function of the amount of the compound required per dose, its stability, release characteristics and other pharmaceutical parameters. Generally, the oral pharmaceutical composition should comprise from about 5% to about 50% of the compound of the subject invention.

The preferred method of injectable administration is via a sterile aqueous solution of pH from about 3 to about 8 (more preferred is pH of from about 3 to about 6) or as a sterile emulsion.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

ORAL DOSE FORMS

Example I

A composition for oral administration is prepared by combining the following ingredients:

| | |
|---|---|
| 1-myristoyl-2-fluoro-2-deoxy-glycerol-3-phosphate, calcium salt | 1.10 kg |
| Sesame oil | 6.50 liters |

The LPA derivative is dissolved in the sesame oil with the aid of sonication and is packaged in soft gelatin capsules using methods known in the art. Two of the resulting capsules, each containing 50 mg of the active, are administered to a 60 kg human in need of treatment.

Example II

A composition for oral administration is prepared by combining the following ingredients:

| | |
|---|---|
| Oleyl lysophosphatidic Acid | 250 g |
| Propylene glycol | 1800 ml |
| Ethyl alcohol | 175 ml |
| Distilled water | 75 ml |
| Artificial Cherry flavor | 10 ml |
| FD&C Red #40 | 0.2 g |

The above ingredients are combined to produce a syrup and are packaged under sterile conditions in 6 oz. bottles. One teaspoon of this formulation is administered to a 70 kg adult human.

Example III

Tablets are prepared by conventional methods, such as mixing and direct compaction, formulated as follows:

| Ingredient | mg per tablet |
|---|---|
| Myristoyl lysophosphatidic acid | 100 |
| Microcrystalline cellulose | 100 |
| Sodium Starch glycolate | 30 |
| Magnesium stearates | 5 |

One tablet is administered orally to a patient in need of treatment two times daily.

INJECTABLE DOSE FORMS

Example IV

Injectable compositions are prepared as follows by combining the respective ingredients using conventional mixing techniques:

| Component | Weight % |
|---|---|
| Composition 1: | |
| 1-palmitoleyl-2-deoxy-glycerol-3-phosphate | 0.05% |
| Aqueous Acetic Acid (1.30%) | 95.45% |
| Dextrose | 4.50% |
| Composition 2: | |
| Oleyl lysophosphatidic acid | 0.05% |
| Aqueous Sodium Acetate (1.18%) | 85.95% |
| Aqueous Acetic Acid (2.0%) | 10.00% |
| Benzyl Alcohol | 4.00% |
| Composition 3: | |
| 1-myristyl-2-fluoro-2-deoxy-glycerol-3-phosphate, calcium salt | 0.05% |
| Propylene Glycol | 99.95% |
| Composition 4: | |
| Palmitoleyl lysophosphatidic acid | 0.05% |
| Polyethylene Glycol: Propylene Glycol (1:3) | 99.95% |

A patient in need of treatment is injected once daily with 25 mls of the composition of concentration 0.4 mg/ml.

TOPICAL DOSE FORMS

Example V

A topical composition is prepared by combining the following components utilizing conventional mixing techniques.

| Ingredients | % Weight |
|---|---|
| Ethanol | 99.87 |
| Oleyl lysophosphatidic acid | 0.13 |

In a suitable vessel, the LPA derivative is dissolved in the ethanol with stirring. This composition is useful for topical application to treat skin cancer or psoriasis. Use of an amount of the composition to deposit about 0.02 mg/cm$^2$ of the active agent to the skin is appropriate. The composition is applied twice daily.

Example VI

A topical composition is prepared by combining the following components utilizing conventional mixing techniques.

| Ingredients | % Weight |
|---|---|
| Ethanol | 99.87 |
| 1-myristoyl-2-chloro-2-deoxy-glycerol-3-phosphate | 0.13 |

In a suitable vessel, the LPA derivative is dissolved in the ethanol with stirring. This composition is useful for topical application to treat skin cancer. Use of an amount of the composition to deposit about 0.06 mg/cm$^2$ of the active agent to the skin is appropriate. The composition is applied once daily.

Example VII

A topical composition is prepared by combining the following components utilizing conventional mixing techniques.

| Ingredients | % Weight |
|---|---|
| Ethanol | 49.00 |
| Propylene glycol | 25.00 |
| Deionized water | 25.00 |
| 1-myristyl-2-fluoro-2-deoxy-glycerol-3-phosphate, calcium salt | 1.00 |

In a suitable vessel, the LPA derivative is dissolved in the ethanol with stirring. Propylene glycol and deionized water are added with stirring. This composition is useful for topical application to treat skin cancer. Use of an amount of the composition to deposit about 0.05 mg/cm$^2$ of the active agent to the skin is appropriate. The composition is applied twice daily.

Example VII

A nonionic oil-in-water emulsion is prepared by combining the following components utilizing conventional mixing techniques:

| Ingredient | % Weight |
| --- | --- |
| Deionized Water | 79.73 |
| Propylene Glycol | 3.00 |
| Octyl Methoxycinnamate | 7.50 |
| Cetyl Alcohol | 2.50 |
| Stearyl Alcohol | 2.50 |
| Laureth 23 | 2.00 |
| C$_{12-15}$ Alcohols Benzoate | 2.00 |
| EDTA | 0.37 |
| Methylparaben | 0.20 |
| Propylparaben | 0.10 |
| 1-Palmitoleyl-2-deoxy-glycerol-3-phosphate | 0.10 |

This composition is useful for topical application to treat skin cancer. Use of an amount of the composition sufficient to deposit about 0.04 mg/cm$^2$ skin of the active agent is appropriate. The composition is applied twice daily.

Example IX

A nonionic oil-in-water emulsion is prepared by combining the following components utilizing conventional mixing techniques:

| Component | Percent by Weight Of Composition |
| --- | --- |
| Deionized Water | 79.73 |
| Propylene Glycol | 3.00 |
| Octyl Methoxycinnamate | 7.50 |
| Cetyl Alcohol | 2.50 |
| Stearyl Alcohol | 2.50 |
| Laureth 23 | 2.00 |
| C$_{12}$-C$_{15}$ Alcohols Benzoate | 2.00 |
| EDTA | 0.37 |
| Methylparaben | 0.20 |
| Propylparaben | 0.10 |
| 1-palmitoleyl-2-deoxy-glycerol-3-phosphate | 0.10 |

This composition is useful for topical application to treat skin cancer. Use of an amount of the composition sufficient to deposit about 0.05 mg/cm$^2$ of the active agent to the skin is appropriate. The composition is applied once daily.

Example X

An ion pair oil-in-water emulsion is prepared by combining the following components utilizing conventional mixing techniques.

| Component | Percent by Weight of Composition |
| --- | --- |
| Deionized Water | 78.05 |
| Permulon TR-2 (C10–C30 Acrylate Copolymer, B. F. Goodrich) | 0.30 |
| Distearyl Dimethyl Ammonium Chloride | 0.15 |
| 1-oleoyl-2-fluoro-2-deoxy-glycerol-3-phosphate, calcium salt | 1.00 |
| 4-N,N-(2-ethylhexyl)methylaminobenzoic acid 4-ester of 2-hydroxy-4-(2-hydroxyethoxy)benzophenone | 4.00 |
| 4-N,N-(2-ethylhexyl)methylaminobenzoic acid ester of 4-(2-hydroxyethoxy)-dibenzoylmethane | 2.00 |
| Dimethyl Isosorbide | 6.00 |
| Dioctyl Malate | 6.00 |
| Cetyl Alcohol | 1.00 |
| Stearyl Alcohol | 1.00 |
| 99% Triethanolamine | 0.50 |

This composition is useful for topical application to treat skin cancer. Use of an amount of the composition sufficient to deposit about 0.2 mg/cm$^2$ of the active agent to the skin is appropriate. The composition is applied twice daily.

Example XI

A sunscreen composition is prepared by combining the following components utilizing conventional mixing techniques.

| Component | Percent by Weight of Composition |
| --- | --- |
| Polypropylene Glycol 15 Stearyl Ether | 15.00 |
| Sorbitan Oleate | 2.00 |
| Octyl Methoxy Cinnamate | 7.50 |
| 1-myristoyl-2-fluoro-2-deoxy-glycerol-3-phosphate, calcium salt | 0.50 |
| Propyl Paraben | 0.15 |
| Butylated Hydroxy Toluene | 0.05 |
| Cyclomethicone | 20.00 |
| Sesame Oil | 5.00 |
| Mineral Oil (Blandol) | 49.80 |

This composition is useful for topical application to treat skin cancer. Use of an amount of the composition is sufficient to deposit about 0.1 mg/cm$^2$ of the active agent to the skin is appropriate. This composition is applied three times daily.

Example XII

| Component | Percent by Weight of Composition |
| --- | --- |
| Deionized Water | 97.63 |
| 1-lauroyl-2-fluro-2-deoxy-glycerol-3-phosphate | 2.00 |
| EDTA | 0.37 |

This composition is useful for topical application to treat skin cancer and psoriasis. Use of an amount of the composition to deposit about 0.5 mg/cm$^2$ of the active agent to the skin is appropriate. The composition is applied once daily.

Example XIII

An anti-dandruff shampoo is prepared by combining the following ingredients using conventional mixing techniques:

| Ingredients | % Weight |
| --- | --- |
| Ammonium Alkyl Sulfate (29% Aqueous Solution) | 55.25 |
| 1-oleoyl-2-fluoro-2-deoxy-glycerol-3-phosphate calcium salt | 2.0 |
| Coconut Monoethanolamide | 3.0 |
| Ethylene Glycol Distearate | 5.0 |
| Sodium Citrate | 0.5 |
| Citric Acid | 0.2 |
| Color Solution | 0.1 |
| Perfume | 0.5 |
| Water q.s. | 100.00 |

The composition is applied continually, once a day, to help existing dandruff subside and prevent or retard the onset of dandruff. Use of an amount of the composition to deposit about 0.50 mg/cm$^2$ of the LPA derivative to the skin is appropriate.

Example XIV

A cream shampoo is prepared by combining the following ingredients using conventional mixing techniques:

| Ingredients | % Weight |
| --- | --- |
| Sodium Alkyl Glyceryl Sulfonate | 60.0 |
| Sodium Chloride | 5.0 |
| Sodium N-Lauroyl Sarcosinate | 12.0 |
| N-Cocoyl Sarcosine Acid | 1.0 |
| Lauric Dethanolamide | 2.0 |
| Myristyl Lysophosphatidic Acid | 2.0 |
| Perfume | 0.5 |
| Color Solution | 0.12 |
| Water q.s. | 100.00 |

The composition is applied continually, once every other three days, to help existing dandruff subside and prevent or retard the onset of dandruff. Use of an amount of the composition to deposit about 0.75 mg/cm$^2$ of the LPA derivative to the skin is appropriate.

Example XV

A cream rinse is prepared by combining the following ingredients using conventional mixing techniques:

| Ingredients | % Weight |
| --- | --- |
| Stearalkonium Chloride | 0.75 |
| Stearyl Alcohol | 0.5 |
| 1-Myristyl-2-Fluoro-2-Deoxy-Glycerol-3-Phosphate Calcium Salt | 0.3 |
| Cetyl Alcohol | 0.5 |
| Polyoxyethylene (2) Cetyl Ether | 0.8 |
| Sodium Chloride | 0.25 |
| Color Solution | 0.2 |
| Perfume | 0.25 |
| Water q.s. | 100.00 |

The composition is applied continually, once every other day, to help existing dandruff subside and prevent or retard the onset of dandruff. Use of an amount of the composition to deposit about 0.10 mg/cm$^2$ of the LPA derivative to the skin is appropriate.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of inhibiting benign epithelial cell proliferation in mammalian cells comprising administering to a human or lower animal susceptible to or having said epithelial cell proliferation a safe and effective amount of a lysophosphatidic acid compound having the structure:

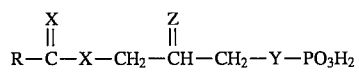

or a cyclic derivative thereof having the structure:

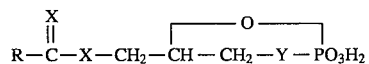

or a pharmaceutically acceptable salt thereof, wherein:

a) —Y— is —O— or —CH$_2$;

b) —Z is —XH, —H or halo;

c) each —X— is independently —O— or —S—; and d) —R is unsubstituted or substituted with a substituent selected from the group consisting of halogen, hydroxy, phenyl, amino and acylamino, saturated or unsaturated, straight or branched chain alkyl having from 11 to about 23 carbon atoms.

2. The method of claim 1 wherein the hyperproliferative condition is psoriasis, and —R has from 13 to about 19 carbon atoms.

3. The method of claim 1 wherein the condition being treated is psoriasis, and —R has from 13 to about 19 carbon atoms.

4. The method of claim 1 wherein the lysophosphatidic acid compound is applied topically to the mammalian skin.

5. The method of claim 4 wherein the amount of lysophosphatidic acid compound applied is from about 0.01 mg per cm$^2$ skin to about 1 mg per cm$^2$ skin, and —R has from 13 to about 19 carbon atoms.

6. The method of claim 1 wherein the composition is administered in an injectable dose form.

7. The method of claim 1 wherein the composition is administered in an oral dose form.

* * * * *

UNITED STATES PATENT AND TRADEMARK OFFICE
CERTIFICATE OF CORRECTION

PATENT NO. : 5,565,439

DATED : 10/15/96

INVENTOR(S) : Piazza et al..

It is certified that error appears in the above-identified patent and that said Letters Patent is hereby corrected as shown below:

In Col. 8, line 63, "Reminigton's" should read --Remington's--.

In Col. 8, line 63, "Science" should read --Sciences--.

In Col. 9, line 8, "Form" should read --Forms--.

In Col. 9, line 41, before "01%" insert --.--.

In Col. 11, line 6, delete the second occurrence of "in-silicone".

In Col. 15, line 42, "trillsate" should read --trilisate--.

In Col. 16, line 8, "butyphenol" should read --butylphenol--.

In Col. 16, line 11, "2,6-t-butylphenol" should read --2,6-d-t-butylphenol--.

In Col. 19, line 66, "0,005" should read --0.005--.

In Col. 26, line 40, claim 2, cancel "hyperproliferative".

In Col. 26, line 41, claim 2, after "condition" insert --being treated--.

In Col. 26, line 43, cancel "Claim 3" and substitute

UNITED STATES PATENT AND TRADEMARK OFFICE
CERTIFICATE OF CORRECTION

PATENT NO. : 5,565,439
DATED : 10/15/96
INVENTOR(S) : Piazza et al..

It is certified that error appears in the above-identified patent and that said Letters Patent is hereby corrected as shown below:

--3. The method of Claim 2 wherein
   (a) -Z is -Cl or -F;
   (b) -R is selected from the group consisting of oleyl, palmitoleyl, palmityl and myristyl;
   (c) -X- is -O-; and
   (d) -Y- is -O-.--.

Signed and Sealed this

Twenty-fifth Day of January, 2000

Attest:

Attesting Officer

*Acting Commissioner of Patents and Trademarks*